United States Patent [19]
Ohkoshi et al.

[11] Patent Number: 6,018,077
[45] Date of Patent: Jan. 25, 2000

[54] PROCESS FOR PRODUCING 2,6-NAPHTHALENEDICARBOXYLIC ACID

[75] Inventors: Fumio Ohkoshi; Hiroshi Ogawa; Kazuo Tanaka; Masato Inari; Hiroshi Machida, all of Okayama-ken, Japan

[73] Assignee: Mitsubishi Gas Chemical Company, Inc., Tokyo, Japan

[21] Appl. No.: 09/048,494

[22] Filed: Mar. 26, 1998

[30] Foreign Application Priority Data

Apr. 17, 1997 [JP] Japan ................................ 9-100415
May 21, 1997 [JP] Japan ................................ 9-131033

[51] Int. Cl.⁷ .................................................. C07C 51/16
[52] U.S. Cl. .......................................... 562/414; 562/412
[58] Field of Search ..................... 562/414, 412

[56] References Cited

U.S. PATENT DOCUMENTS

| | | |
|---|---|---|
| 3,856,855 | 12/1974 | Yamashita et al. . |
| 4,933,491 | 6/1990 | Albertins et al. . |
| 5,183,933 | 2/1993 | Harper et al. . |
| 5,292,934 | 3/1994 | Sikkenga et al. ........................ 562/413 |

OTHER PUBLICATIONS

Database WPI, Section Ch, Week 9502, Derwent Publications Ltd., London, GB, Class A41, AN 95–009584 of JP 06 293 697 A, Oct. 1994.

*Primary Examiner*—Paul J. Killos
*Assistant Examiner*—J. Parsa
*Attorney, Agent, or Firm*—Frishauf, Holtz, Goodman, Langer & Chick, P.C.

[57] ABSTRACT

A process for producing 2,6-naphthalenedicarboxylic acid comprising oxidizing 2,6-dimethylnaphthalene with a gas containing oxygen in a solvent comprising a lower aliphatic carboxylic acid in the presence of a catalyst comprising cobalt, manganese, and bromine, wherein the total amount of cobalt and manganese in the catalyst is 50 to 300 mg atom per 1 g mol of 2,6-dimethylnaphthalene, a ratio by g atom of manganese to cobalt in the catalyst is 20:1 to 4:1, and the oxidation is conducted at a temperature of 200 to 250° C.; and a process as described above, wherein a mother liquor which is obtained from a slurry of a product of the oxidation via a step of solid-liquid separation is recyled to a step of oxidation after heat treatment at a temperature of 150° C. or higher. In accordance with the processes, accumulation of substances which affect the oxidation adversely is prevented. Moreover, a large fraction of a mother liquor of oxidation can be recycled without decrease in the yield of the reaction, and the catalyst components and the solvent components in the mother liquor of oxidation can be utilized efficiently.

20 Claims, 1 Drawing Sheet

PROCESS FOR PRODUCING 2,6-NAPHTHALENEDICARBOXYLIC ACID

BACKGROUND OF THE INVENTION

1. Field of the Invention

The present invention relates to a process for producing 2,6-naphthalenedicarboxylic acid, and more particularly to a process for producing 2,6-naphthalenedicarboxylic acid industrially advantageously by liquid phase oxidation of 2,6-dimethylnaphthalene, wherein a mother liquor which is obtained after separation of crystals of 2,6-naphthalenedicarboxylic acid from a product of the liquid phase oxidation (referred to as a mother liquor of oxidation, hereinafter) is efficiently recycled to the reaction system, and the oxidation catalyst is reused.

2. Description of the Related Arts 2,6-Naphthalenedicarboxylic acid and esters thereof are useful as raw materials for high performance polyesters.

2,6-Naphthalenedicarboxylic acid is produced by oxidation of a 2,6-dialkylnaphthalene in a solvent containing a lower aliphatic carboxylic acid in the presence of a catalyst containing cobalt, manganese, and bromine (U.S. Pat. No. 3,856,855).

In this oxidation, the naphthalene ring itself tends to be oxidized to form trimellitic acid. Trimellitic acid thus formed tends to form strong complexes with the metal catalyst for oxidation, and it is difficult to separate and remove the metals in the complexes from 2,6-naphthalenedicarboxylic acid. A mother liquor of oxidation obtained after separation of crystals of 2,6-naphthalenedicarboxylic acid from the reaction product contains, as described above, trimellitic acid along with the useful metal catalyst for oxidation. Generally in the production of an aromatic carboxylic acid by the liquid phase oxidation of an aromatic hydrocarbon, relatively expensive catalyst components, such as cobalt, manganese, and bromine, are used, and it is economically desirable that the catalyst components are recycled and reused (Japanese Patent Application Laid-Open No. Heisei 4(1992)-266846). However, when the mother liquor of oxidation is recycled into the oxidation system as described above, a problem arises in that trimellitic acid forms complexes with the metal catalyst for oxidation to deactivate the catalyst.

To solve the above problem that the metal catalyst for oxidation is deactivated by trimellitic acid, a process is described in Japanese Patent Application Laid-Open No. Heisei 7(1995)-48314 in which, when 2,6-dimethylnaphthalene is oxidized with a gas containing molecular oxygen in a solution in which a catalyst containing heavy metals and bromine is dissolved in a solvent containing a lower aliphatic carboxylic acid, the catalyst is recycled and reused after the catalyst is supplemented so that the concentration of the heavy metals of the catalyst, excluding the heavy metals in the form of complexes with ortho-benzenedicarboxylic acids, in the solvent is 0.2% by weight or more.

However, the increase in the yield is not sufficient although the catalyst is supplemented so that the concentration of the heavy metals of the catalyst, excluding the heavy metals in the form of complexes with ortho-benzenedicarboxylic acids, in the solvent is 0.2% by weight or more.

As described above, a larger recycled fraction of the mother liquor of oxidation is preferable because, by recycling and reusing the mother liquor of oxidation, the catalyst components and the solvent components in the mother liquor of oxidation can be utilized efficiently and the raw materials, intermediate products, and fine particles of 2,6-naphthalenedicarboxylic acid contained in the mother liquor of oxidation can be recovered. However, the above mother liquor of oxidation contains small amounts of impurities and byproducts in addition to the useful components described above, and substances adversely affecting the oxidation are accumulated by recycling and reusing the mother liquor of oxidation to decrease the yield.

Unlike the commercially established processes for producing terephthalic acid, the process for producing 2,6-naphthalenedicarboxylic acid has a problem in recycling and reusing the mother liquor of oxidation as the solvent for the oxidation in that particles of crystals of 2,6-naphthalenedicarboxylic acid formed in the step of oxidation are very small, and increasing the particle size of the crystals is difficult even by treatments in a plurality of crystallization tanks because solubility of 2,6-naphthalenedicarboxylic acid is very small in the solvent for the reaction. Therefore, it is very difficult that complete separation in the step of solid-liquid separation can be achieved.

As the result, the mother liquor of oxidation contains a portion of crystals of 2,6-naphthalenedicarboxylic acid, particularly crystals having smaller sizes than the average size of crystals grown in the step of oxidation. When the mother liquor of oxidation containing very fine particles is recycled into the reactor for the oxidation and repeatedly used as the solvent for the oxidation, the content of fine crystals in a slurry supplied to the step of solid-liquid separation is increased, and the desired ability of solid-liquid separation cannot be exhibited.

SUMMARY OF THE INVENTION

Accordingly, the present invention has an object of providing a process for producing 2,6-naphthalenedicarboxylic acid which can prevent accumulation of substances adversely affecting the reaction and maintain a high yield when a mother liquor of oxidation is recycled in the liquid phase oxidation of dimethylnaphthalene.

The present invention has another object of providing a process for continuously producing 2,6-naphthalenedicarboxylic acid which, when a mother liquor of oxidation is recycled in the liquid phase oxidation of 2,6-dimethylnaphthalene, exhibits a sufficient ability of separation of crystals even when a recycled fraction of mother liquor of oxidation is increased and shows a high efficiency of production.

As the result of extensive studies by the present inventors to develop a process for producing 2,6-naphthalenedicarboxylic acid which can achieve the above objects, it was found that accumulation of substances adversely affecting the oxidation can be prevented when the oxidation is conducted in a specific catalyst condition, particularly at an increased concentration of manganese, and also when the oxidation is conducted in a specific combination of this catalyst condition and the condition of the oxidation, and a large fraction of the mother liquor of oxidation can be recycled to a reactor for the oxidation without decrease in the yield of 2,6-naphthalenedicarboxylic acid. The present invention has been completed on the basis of this knowledge.

It was also found by the present inventors that, when the mother liquor of oxidation recycled to the reactor for the oxidation is treated by heating at a specific temperature in advance, the ability of solid-liquid separation can be sufficiently maintained for a long period of time even when the recycled fraction of the mother liquor of oxidation is increased.

Accordingly, the present invention provides a process for producing 2,6-naphthalenedicarboxylic acid comprising oxidizing 2,6-dimethylnaphthalene with a gas comprising oxygen in a solvent comprising a lower aliphatic carboxylic acid in the presence of a catalyst comprising cobalt, manganese, and bromine, wherein the total amount of cobalt and manganese in the catalyst is 50 to 300 mg atom per 1 g mol of 2,6-dimethylnaphthalene, a ratio by g atom of manganese to cobalt in the catalyst is 20:1 to 4:1, and the oxidation is conducted at a temperature of 200 to 250° C.

The present invention also provides a process for continuously producing 2,6-naphthalenedicarboxylic acid comprising oxidizing 2,6-dimethylnaphthalene with a gas comprising oxygen in a solvent comprising a lower aliphatic carboxylic acid in the presence of a catalyst comprising cobalt, manganese, and bromine, wherein a mother liquor separated from a slurry of a product of the oxidation in a step of solid-liquid separation is treated by heating at a temperature of 150° C. or higher and then recycled to a step of oxidation.

DESCRIPTION OF THE PREFERRED EMBODIMENTS

Figure 1:
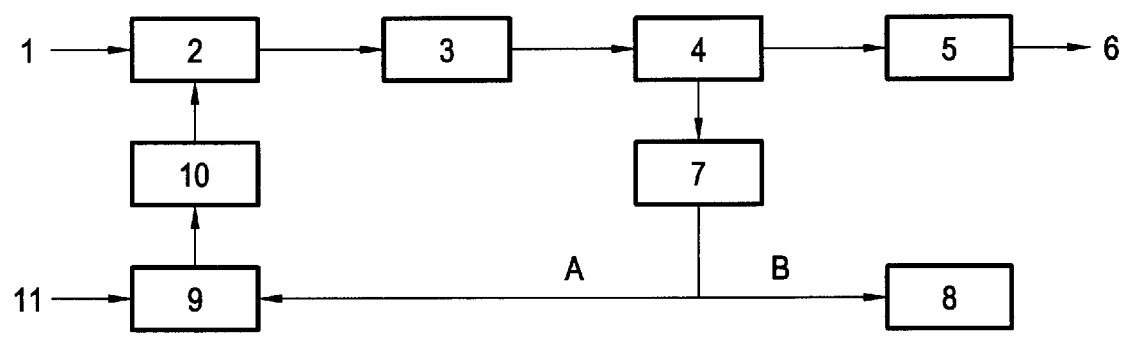
FIG. 1 shows a schematic diagram describing the process for producing 2,6-naphthalenedicarboxylic acid of the present invention.

The present invention is described in more detail in the following.

The purity of 2,6-dimethylnaphthalene used as the raw material for the oxidation in the present invention is preferably 98% by weight or more, more preferably 99% by weight or more. To recycle a large fraction of the mother liquor of oxidation without decrease in the yield, it is preferable that the purity of 2,6-dimethylnaphthalene used as the raw material for the oxidation in the present invention is kept high.

As the solvent for the oxidation, a lower aliphatic carboxylic acid, such as formic acid, acetic acid, propionic acid, butyric acid, and a mixture of these acids, can be used, and acetic acid is preferably used. The solvent may contain water. However, the content of water is 30% by weight or less, preferably 1 to 20% by weight, more preferably 1 to 15% by weight, most preferably 1 to 10% by weight, of the total amount of the lower aliphatic carboxylic acid and water which are added into the field of the oxidation.

As for the amounts of the lower aliphatic carboxylic acid and 2,6-dimethylnaphthalene which are added into the field of the oxidation, the ratio of the lower aliphatic carboxylic acid to 2,6-dimethylnaphthalene is in the range of 1:1 to 20:1, preferably in the range of 2:1 to 12:1, more preferably in the range of 2:1 to 10:1.

As the components of the catalyst for the oxidation, a cobalt compound, a manganese compound, and a bromine compound are used. Compounds of other heavy metals, such as iron, cerium, nickel, and palladium, may be additionally used, where necessary. Preferable examples of the compounds of heavy metals, such as cobalt, manganese, and the like, include salts of organic acids, hydroxides, halides, and carbonates of such heavy metals. Among these compounds, acetates and bromides of the heavy metals are preferable. As the bromine compound, any compound can be used as long as the compound is dissolved in the reaction system and generates a bromine ion. Examples of the bromine compound include inorganic compounds, such as hydrogen bromide, sodium bromide, cobalt bromide, and manganese bromide, and organic compounds, such as bromoacetic acid and terabromoethane. Among these compounds, hydrogen bromide, cobalt bromide, and manganese bromide are preferable.

In the present invention, it is important that the catalyst components be used in suitable amounts to prevent accumulation of substances adversely affecting the reaction, such as trimellitic acid, by recycling of the mother liquor of oxidation.

The amount of the metal catalyst is 30 to 300 mg atom, preferably 50 to 300 mg atom, more preferably 100 to 250 mg atom, as the total amount of cobalt and manganese per 1 g mol of 2,6-dimethylnaphthalene. When the amount of the metal catalyst is less than the above range, the yield of 2,6-naphthalenedicarboxylic acid in the reaction is decreased. When the amount of the metal catalyst exceeds the above range, the amount of the catalyst removed together with the formed 2,6-naphthalenedicarboxylic acid is increased to cause increase in the cost of the catalyst, and the amount is industrially disadvantageous. The above range of the amount of the catalyst is larger by 20 to 40% than the amount of the catalyst used in conventional processes in which a mother liquor of oxidation is not recycled. By using a larger amount of the metal catalyst as described above, the adverse effect of accumulation of substances adversely affecting the reaction, such as trimellitic acid, by recycling the mother liquor of oxidation can be suppressed.

The ratio by g atom of manganese to cobalt in the oxidation catalyst is 20:1 to 4:1, preferably 15:1 to 4:1, more preferably 12:1 to 5:1, most preferably 10:1 to 6:1. In conventional processes for the liquid phase oxidation of 2,6-dimethylnaphthalene, the ratio in g atom of manganese to cobalt is about 3:1. In the present invention, the formation of trimellitic acid can be suppressed by increasing the relative amount of manganese. Moreover, manganese shows a larger tendency to form a complex with trimellitic acid than cobalt does. The formed complex with trimellitic acid is attached to crystals of 2,6-naphthalenedicarboxylic acid and separated from the mother liquor of oxidation together with the crystals. Therefore, the accumulation of trimellitic acid in the oxidation can be suppressed by increasing the relative amount of manganese when the mother liquor of oxidation is recycled.

The metal salt of trimellitic acid can easily be removed from 2,6-naphthalenedicarboxylic acid containing the metal salt by a suitable method, such as conversion of 2,6-naphthalenedicarboxylic acid into an ester of 2,6-naphthalenedicarboxylic acid easily soluble in an organic solvent by esterification with an alcohol, followed by separation of the ester from the insoluble metal salt.

As described above, although the amount of the metal salt accompanied with 2,6-naphthalenedicarboxylic acid is increased by increasing the relative amount of manganese, the step of purification of 2,6-naphthalenedicarboxylic acid is hardly affected by the increase in the amount of the accompanied metal salt because the metal salt can be separated easily, and the mother liquor of oxidation can be recycled advantageously.

The content of the bromine component in the oxidation catalyst is 1 to 500 mg atom, preferably 10 to 300 mg atom, more preferably 15 to 150 mg atom, most preferably 20 to 100 mg atom, per 1 g mol of 2,6-dimethylnaphthalene. When the amount of the bromine component is less than the above range, the yield of 2,6-naphthalenedicarboxylic acid is decreased at larger recycled fractions of the mother liquor of oxidation. When the amount of the bromine component exceeds the above range, compounds containing bromine, such as bromonaphthalenedicarboxylic acid, are formed as byproducts in larger amounts.

As the gas containing oxygen which is used in the present invention, oxygen gas or a gas obtained by mixing oxygen with an inert gas, such as nitrogen and argon, can be used. Air is generally used.

As the reactor for the oxidation, a tank equipped with a stirrer or a tower through which bubbles can be passed is used. To achieve sufficient mixing in the reactor, a tank equipped with a stirrer is preferable.

As the process for the reaction, a semi-batch process or a continuous process is advantageously used. In a semi-batch process, it is preferable that supply of the gas containing oxygen is continued for further 5 to 60 minutes to achieve the complete oxidation after supply of the raw material has been stopped. In a continuous process, it is preferable that a plurality of reactors are connected in series, and the reaction is conducted successively in these reactors to increase the yield of the reaction.

The temperature of the oxidation is 170 to 250° C., preferably 180 to 240° C., more preferably 200 to 240° C.

When the temperature of the oxidation is lower than the above range, substances adversely affecting the reaction are accumulated while recycling of the mother liquor of oxidation is repeated, and the yield of 2,6-naphthalenedicarboxylic acid is decreased. Moreover, large amounts of intermediate products of the reaction, such as 6-formyl-2-naphthoic acid, remain in the reaction product. There is also the possibility that the efficiency of the solid-liquid separation is adversely affected because the size of obtained crystals of 2,6-naphthalenedicarboxylic acid is decreased.

When the temperature of the reaction exceeds the above range, loss of the lower aliphatic carboxylic acid used as the solvent by burning is increased, and the amounts of byproducts, such as naphthalenetricarboxylic acid, is increased.

In other words, it is necessary that the temperature of the reaction be kept in the range satisfying the conditions that substances adversely affecting the reaction are burned, that the size of crystals of 2,6-naphthalenedicarboxylic acid is kept at a specific value or larger, that the yield is not decreased, that intermediate products of the reaction are not left remaining, that byproducts are not increased, and that the loss of the lower aliphatic carboxylic acid used as the solvent by burning is within the allowable range. The temperature of the reaction is very important for recycling the mother liquor of oxidation in accordance with the process of the present invention, and the range described above is advantageously selected.

In the oxidation, the gas containing oxygen is continuously supplied to the reactor and the gas formed during the reaction is continuously discharged so that the pressure is kept at 5 to 40 kg/cm$^2$G, preferably 10 to 30 kg/cm$^2$G. The reactor is equipped with a reflux cooler, and large amounts of the solvent and water formed by the oxidation which are accompanied with the discharged gas are condensed. The condensed solvent and water are generally refluxed to the reactor, but a portion of the condensed solvent and water may occasionally be discharged to the outside of the reaction system to adjust the concentration of water in the reactor. The concentration of oxygen in the vent gas discharged from the reactor is 0.1 to 8% by volume, preferably 0.5 to 5% by volume, more preferably 1 to 5% by volume, based on the dry gas. When the concentration of oxygen in the discharged gas is lower than the above range, unfavorable phenomena, such as increase in intermediate products of the reaction and inferior color of 2,6-naphthalenedicarboxylic acid obtained, take place. When the concentration of oxygen exceeds the above range, unnecessary increase in the cost of a compressor for the gas occurs.

The through-put (the amount added to the unit amount of the liquid in the reactor per unit time) of 2,6-dimethylnaphthalene used as the raw material in the reactor for the oxidation is 50 to 500 kg/m$^3$. The through-put can be used as a measure of productivity of the reactor. 2,6-Naphthalenedicarboxylic acid formed by the oxidation is obtained as a slurry. The slurry is generally cooled under a reduced pressure, treated in a crystallization tank, and then separated into 2,6-naphthalenedicarboxylic acid and a mother liquor of oxidation in an apparatus for solid-liquid separation.

The mother liquor of oxidation contains many useful components, such as the lower aliphatic carboxylic acid used as the solvent, water, the metal catalysts and the bromine compound used for the oxidation, unreacted 2,6-dimethylnaphthalene, and intermediate products of the oxidation. Substances adversely affecting the reaction, such as trimellitic acid, are also contained.

By the combination of the specific conditions for the catalyst and the specific conditions for the oxidation as shown in the present invention, 40% or more of the mother liquor of oxidation obtained after separation of crystals of 2,6-naphthalenedicarboxylic acid can be recycled directly into the reactor for the oxidation. About 100% of the mother liquor of oxidation may be recycled, where necessary.

Metal complexes of trimellitic acid accompanied with the crystals of 2,6-naphthalenedicarboxylic acid can be easily separated as insoluble matters after converting 2,6-naphthalenedicarboxylic acid into an ester of 2,6-naphthalenedicarboxylic acid easily soluble in organic solvents by esterification with an alcohol.

During the esterification reaction of 2,6-naphthalenedicarboxylic acid, metal salts of trimellitic acid and the like are converted into metal salts of 2,6-naphthalenedicarboxylic acid. Therefore, trimellitic acid is not accumulated even when the insoluble metal salts are recycled to the oxidation without particular treatments, and manganese and cobalt can be recovered advantageously.

A schematic diagram describing the process for producing 2,6-naphthalenedicarboxylic acid of the present invention is shown in FIG. 1. In FIG. 1, 2,6-dimethylnaphthalene used as the raw material is introduced into a step of oxidation 2 through a path 1, and the oxidation with a gas containing oxygen is conducted in a solvent containing a low aliphatic carboxylic acid in the presence of a catalyst comprising heavy metals and bromine. A slurry of a product of the oxidation from the step of oxidation 2 is transferred to a step of crystallization 3 and then to a step of solid-liquid separation 4. Crystals are separated in the step of solid-liquid separation and transferred to a step of drying 5 to obtain a crude 2,6-naphthalenedicarboxylic acid. A mother liquor of oxidation separated in the step of solid-liquid separation is introduced into a tank for a mother liquor of oxidation 7. A portion of the mother liquor of oxidation is transferred to a step of recovery 8, and the catalyst components and the solvent are recovered. Into the remaining portion of the mother liquor of oxidation placed in a preparation tank 9, the catalyst components are added through a path 11 to prepare the catalyst. The obtained mixture is transferred to a tank for a heat treatment 10 and then recycled to the step of oxidation 2.

In FIG. 1, the recycled fraction of a mother liquor of oxidation is defined as follows:

Recycled fraction of a mother liquor of oxidation=A/(A+B)×100 (%) wherein

A represents the amount (kg/h) of the mother liquor of oxidation transferred to the preparation tank 9 from the tank for a mother liquor of oxidation 7, and B represents the amount (kg/h) of the mother liquor of oxidation transferred to the step of recovery 8 from the tank for a mother liquor of oxidation 7.

As described above, it is preferable that the fluid coming out of the reactor for the oxidation which contains 2,6-naphthalenedicarboxylic acid formed in the reactor for the oxidation is transferred to another reactor for the oxidation which is connected to the first reactor in series, and the oxidation is completed with a gas containing oxygen in the second reactor. The slurry of the product of the oxidation is preferably transferred to the following step of crystallization in which one or more tanks for crystallization are connected to each other in series and then to the step of solid-liquid separation after the pressure is released and the product is cooled.

In the step of solid-liquid separation, the slurry containing 2,6-naphthalenedicarboxylic acid formed in the step of oxidation is separated into crystals and a mother liquor of oxidation by the use of the apparatus for the solid-liquid separation. The solid-liquid separation is generally conducted under an atmospheric pressure. The temperature of separation is not particularly limited, and the separation generally conducted at a temperature lower than the boiling point of the solvent under an atmospheric pressure, i.e., in the range of about 50 to 110° C.

Examples of the apparatus for the solid-liquid separation include centrifuges, centrifugal filters, and vacuum filters. Because particle diameters of crystals of 2,6-naphthalenedicarboxylic acid is very small, a decanter type centrifuge which can efficiently collect crystals having small diameters is generally used.

One of the present inventions relates to a treatment of the mother liquor of oxidation containing fine crystals which have leaked into the mother liquor of oxidation in the step of solid-liquid separation.

The distribution of particle size of crystals in the slurry supplied to the step of solid-liquid separation cannot generally be described because the distribution depends on the conditions in the step of oxidation, the presence or the absence of a crystallization tank, the conditions of the crystallization tank when it is present, and factors for operation of the apparatus for solid-liquid separation. In an example in which the mother liquor of oxidation is not recycled into the reactor for the oxidation, the particle size of crystals has the following distribution:

| | |
|---|---|
| 1 $\mu$m or smaller | 1.4% |
| 1 to 5 $\mu$m | 14.4% |
| 5 to 10 $\mu$m | 11.7% |
| 10 to 20 $\mu$m | 21.3% |
| 20 to 30 $\mu$m | 20.1% |
| 30 to 50 $\mu$m | 22.4% |
| 50 $\mu$m or larger | 8.7% | wherein the diameter of crystals is measured by a laser diffraction type apparatus for measurement of particle diameter distribution.

In a decanter type centrifuge, it is generally considered that particles having a diameter of several micrometer or larger can be collected. The above distribution shows that considerable amounts of particles having smaller size than the several micrometer are contained in the slurry supplied to the apparatus for solid-liquid separation. Therefore, it is the real situation that a portion of fine crystals inevitably leaks into the mother liquor of oxidation coming out of the apparatus for solid-liquid separation.

The amount of fine crystals leaking into the mother liquor of oxidation is varied depending on the distribution of particle size of crystals in the slurry, basic properties and operating conditions of the apparatus for solid-liquid separation, and the amount of the slurry supplied to the apparatus for solid-liquid separation. In an example in which the mother liquor of oxidation is not recycled into the reactor for the oxidation, the amount of fine crystals leaking into the mother liquor of oxidation is about 1% by weight of the mother liquor.

A portion of the mother liquor of oxidation coming out of the step of solid-liquid separation is transferred to the step of recovery to recover the solvent and the catalyst. The remaining portion of the mother liquor of oxidation is transferred for recycling to a preparation tank which is used for preparing the solvent for the oxidation. In the preparation tank, necessary amounts of the solvent and the catalyst are added to the mother liquor of oxidation to prepare the solvent for the oxidation, and the prepared solvent for the oxidation is transferred to the reactor for the oxidation.

A method of supplying 2,6-dimethylnaphthalene used as the raw material to the preparation tank and then to the reactor for the oxidation after being mixed with the solvent in the preparation tank in advance may be used. However, there is the possibility that unfavorable changes take place in the preparation tank or during transfer to the reactor for the oxidation. Therefore, it is preferable that 2,6-dimethylnaphthalene used as the raw material is directly transferred to the reactor for the oxidation separately.

In accordance with the process of the present invention, it is preferable that, after a portion of the mother liquor of oxidation has been transferred to the step of recovery, the remaining mother liquor of oxidation is treated by heating and then supplied to the reactor for the oxidation. The liquid at the upstream of the preparation tank, i.e., the mother liquor of oxidation before being supplied to the preparation tank, may be treated by heating. However, it is preferable that the liquid at the downstream of the preparation tank, i.e., the solvent for the oxidation which is prepared in the preparation tank and to be supplied to the reactor for the oxidation, is treated by heating.

In the step of heat treatment, the liquid is generally allowed to stay in a tank for a heat treatment for a specific period of time. The liquid may also be allowed to stay in a pipe for transfer of the liquid for a specific period of time. In either method, it is necessary that the heat treatment be conducted at a temperature of 150° C. or higher, preferably 160 to 240° C.

The time of the heat treatment is preferably 3 minutes or more. As shown in the examples, 100% of the mother liquor of oxidation can be recycled even when the time of the heat treatment is as short as about 5 minutes.

When the mother liquor of oxidation is recycled to the reactor for the oxidation without any heat treatment or with a heat treatment at an excessively low temperature, the amount of fine crystals leaking into the separated mother liquor of oxidation is gradually increased with increase in the time of the continuous operation, and serious troubles may occasionally take place when the production is continued for a long period of time. Therefore, in processes using conventional apparatuses for producing 2,6-naphthalenedicarboxylic acid, the recycled fraction of the mother liquor of oxidation remains at about 30% at most. In contrast, the recycled fraction of the mother liquor of oxidation can be increased to 40% or more in accordance with the process of the present invention.

It is described in Japanese Patent Application Laid-Open No. Heisei 6(1994)-293697 that, when fine crystals leaking into the mother liquor of oxidation are supplied to the reactor for the oxidation without any treatment, larger crystals of 2,6-naphthalenedicarboxylic acid are obtained. However, such a phenomenon could never be observed in the experimental continuous production conducted by the present inventors. This difference is considered to arise because the invention described in Japanese Patent Application Laid-Open No. Heisei 6(1994)-293697 was obtained on the basis of the results of experiments using a batch-type facility. At least in experiments using continuous facilities, it is apparent that, when the mother liquor of oxidation containing fine crystals is supplied to the reactor for the oxidation without any treatment, serious troubles in the smooth operation take place in the step of solid-liquid separation and also in the step of the oxidation with increase in the time of the continuous operation.

As described above in detail, in the liquid phase oxidation of dimethylnaphthalene, accumulation of substances adversely affecting the oxidation can be prevented by combination of the specific catalyst conditions, particularly the increased concentration of manganese, with the conditions of the oxidation in accordance with the process of the present invention, and a large fraction of the mother liquor of oxidation can be recycled without decrease in the yield.

By recycling the mother liquor of oxidation, the catalyst components and the solvent components in the mother liquor of oxidation can be utilized efficiently, and the raw materials, intermediate products, and fine particles of 2,6-naphthalenedicarboxylic acid contained in the mother liquor of oxidation can be recovered.

Moreover, by recycling the mother liquor of oxidation separated from the slurry of the product of the oxidation in the step of solid-liquid separation after the heat treatment in accordance with the process of the present invention, a sufficient ability for separation of crystals can be exhibited even when the recycled fraction of the mother liquor of oxidation is increased. Therefore, the load in the step of recovery is remarkably decreased, and losses in the solvent and the catalyst can also be decreased.

Thus, the process of the present invention has a remarkable industrial significance because 2,6-naphthalenedicarboxylic acid can efficiently be produced industrially advantageously in accordance with the process of the present invention.

EXAMPLES

The present invention is described specifically with reference to examples in the following. However, the present invention is not limited by the examples.

In the following Examples, Comparative Examples, and Reference Examples, the entire mother liquor of oxidation obtained was reused in the recycling test. The metal salts attached to crystals were supplemented by adding cobalt acetate tetrahydrate and manganese acetate tetrahydrate. To supplement bromine, hydrobromic acid was added in such an amount that the concentration of bromine ion was kept constant.

The following abbreviations are used in the Examples and Comparative Examples:
NDCA: 2,6-naphthalenedicarboxylic acid
TMA: trimellitic acid
FNA: formylnaphthoic acid Example 1

Into a 2,000 ml autoclave made of titanium and equipped with an inlet for raw materials, an inlet for a solvent, an inlet for a gas, an outlet for a gas, an outlet for the reaction product, a reflux cooler, an electromagnetic stirrer, a heater, and an instrument for detecting the liquid surface; acetic acid, cobalt acetate tetrahydrate, manganese acetate tetrahydrate, a 47% by weight aqueous solution of hydrogen bromide, and water were added and mixed together to prepare 650 g of a catalyst solution containing 0.1% by weight of cobalt, 0.6% by weight of manganese, 0.5% by weight of bromine, and 3% by weight of water. Then, nitrogen gas was introduced from the inlet for a gas to adjust the pressure inside the autoclave to 20 kg/cm$^2$, and the prepared mixture was heated to 220° C. by the heater.

After the temperature and the pressure were stabilized, 2,6-dimethylnaphthalene having a purity of 99.4% by weight, was introduced into the autoclave at a flow rate of 20 g/h, and a catalyst solution having the same composition as that described above was introduced into the autoclave at a flow rate of 720 g/h. At the same time, the air was introduced into the autoclave so that the concentration of oxygen in a vent gas discharged from the outlet for a gas was adjusted to 3%.

Fifteen minutes after starting introducing 2,6-dimethylnaphthalene and the catalyst solution, discharge of the reaction mixture was started. The supply of the solution of the raw material and the catalyst solution was continued for 8 hours while the liquid surface was kept at the same position. The discharged reaction mixture was separated into crystals and a mother liquor of oxidation by filtration at 70 to 80° C. The obtained crystals were dried and analyzed.

The mother liquor of oxidation was analyzed. Water formed by the oxidation was vaporized and cobalt, manganese, and bromine which were attached to the crystals and lost were supplemented to adjust the concentrations of cobalt, manganese, and bromine to the same values as those of the above catalyst solution. The mother liquor of oxidation thus prepared was used for the next run of the recycling test. The recycling test was conducted by repeating these procedures. The yield of NDCA and the amounts of TMA and FNA were obtained by the analysis of the obtained crystals and the mother liquor of oxidation and are shown in Table 1.

TABLE 1

| Number of recycling | 0 | 1 | 2 | 3 | 4 |
|---|---|---|---|---|---|
| NDCA (% by mol) | 93.9 | 93.1 | 93.5 | 92.8 | 92.8 |
| TMA (% by mol) | 1.98 | 2.49 | 2.36 | 2.56 | 2.50 |
| FNA (% by mol) | 0.20 | 0.24 | 0.19 | 0.20 | 0.20 |

In Example 1, the total amount of cobalt and manganese was 118 mg atom per 1 g mol of 2,6-dimethylnaphthalene, and the ratio by g atom of manganese to cobalt was 6.43:1. The results in Table 1 show that, even when the mother liquor of oxidation was recycled 4 times, the yield of NDCA was little decreased, and the amount of TMA formed as a byproduct was approximately constant.

Comparative Example 1

The recycling test was repeated in accordance with the same procedures as those conducted in Example 1 except that the catalyst solution contained 0.24% by weight of cobalt, 0.47% by weight of manganese, 0.5% by weight of bromine, and 3% by weight of water. The results are shown in Table 2.

TABLE 2

| Number of recycling | 0 | 1 | 2 | 3 |
|---|---|---|---|---|
| NDCA (% by mol) | 93.21 | 92.19 | 91.50 | 90.31 |
| TMA (% by mol) | 2.23 | 3.18 | 3.70 | 4.36 |
| FNA (% by mol) | 0.51 | 0.58 | 0.81 | 0.78 |

In Comparative Example 1, the total amount of cobalt and manganese was 118 mg atom per 1 g mol of 2,6-dimethylnaphthalene, and the ratio by g atom of manganese to cobalt was 2.12:1. The results in Table 2 show that, when the mother liquor of oxidation was repeatedly recycled, the content of FNA was increased, the formation of TMA as a byproduct was also increased, and the yield of NDCA was decreased.

Example 2

The recycling test was repeated in accordance with the same procedures as those conducted in Example 1 except that the catalyst solution contained 0.12% by weight of cobalt, 0.9% by weight of manganese, 0.5% by weight of bromine, and 3% by weight of water, and the catalyst solution was supplied at a flow rate of 480 kg/h. The results are shown in Table 3.

TABLE 3

| Number of recycling | 0 | 1 | 2 | 3 | 4 |
|---|---|---|---|---|---|
| NDCA (% by mol) | 93.7 | 93.3 | 93.0 | 92.5 | 92.5 |
| TMA (% by mol) | 2.23 | 2.76 | 2.91 | 3.13 | 3.00 |
| FNA (% by mol) | 0.19 | 0.24 | 0.48 | 0.17 | 0.20 |

In Example 2, the total amount of cobalt and manganese was 115 mg atom per 1 g mol of 2,6-dimethylnaphthalene, and the ratio by g atom of manganese to cobalt was 8.04:1. The results in Table 1 show that, even when the mother liquor of oxidation was recycled 4 times, the yield of NDCA was little decreased, and the amount of TMA formed as a byproduct was approximately constant.

Comparative Example 2

The recycling test was repeated in accordance with the same procedures as those conducted in Example 1 except that the temperature of the reaction was 195° C. and the pressure of the reaction was 18 kg/cm²G. The results are shown in Table 4.

TABLE 4

| Number of recycling | 0 | 1 | 2 | 3 | 4 |
|---|---|---|---|---|---|
| NDCA (% by mol) | 92.5 | 91.6 | 90.9 | 89.8 | 89.8 |
| TMA (% by mol) | 3.22 | 3.67 | 4.23 | 4.76 | 5.03 |
| FNA (% by mol) | 0.66 | 0.24 | 0.48 | 0.17 | 0.40 |

The results in Table 4 show that, when the temperature of the reaction was set at 195° C., the formation of TMA as a byproduct was increased and the yield of NDCA was decreased by repeatedly recycling the mother liquor of oxidation.

Examples 3 to 6 and Reference Examples 1 and 2

An autoclave which was made of titanium, had an inner volume of 60 liter, and was equipped with an apparatus for stirring, a reflux cooler, an inlet for 2,6-diimethylnaphthalene used as the raw material, an inlet for a solvent, an inlet for the air, an outlet tube for the reaction product, and an external heater was used as the reactor for the oxidation, and 2,6-naphthalenedicarboxylic acid was produced continuously. The surface of the reaction mixture was always controlled at the position of about 50% of the reactor. 2,6-Dimethylnaphthalene was heated to about 130° C. so that it is kept in the liquid state and supplied to the reactor for the oxidation by a piston type pump. A solvent was mixed with catalyst components in a preparation tank in advance and supplied to the reactor for the oxidation by another piston type pump. The preparation tank was adjusted to a specific temperature by heating using the external heater. The amounts of 2,6-dimethylnaphthalene used as the raw material and the amount of the solvent supplied to the reactor for the oxidation and the composition of the solvent were as follows:

| | |
|---|---|
| the amount of 2,6-dimethylnaphthalene | 100 parts by weight |
| the amount of the solvent | 500 parts by weight |
| the composition of the solvent | |
| water | 5% |
| manganese | 8000 ppm |
| cobalt | 1200 ppm |
| Br | 5000 ppm |
| acetic acid | the remaining portion |

Manganese, cobalt, and bromine were added as manganese acetate tetrahydrate, cobalt acetate tetrahydrate, and hydrobromic acid, respectively. A compressed air was supplied to the reactor for the oxidation at such a flow rate that the concentration of oxygen in the vent gas discharged from the reactor for the oxidation was in the range of 1.8 to 2.2%. The temperature of the oxidation was adjusted by the external heater so that a thermometer inserted at a lower position in the middle part of the reactor for the oxidation showed a temperature of 210° C. The pressure of the oxidation was adjusted by a valve for adjusting the pressure disposed at a downstream position of the reflux condenser so that a pressure gauge disposed at a downstream position of the reflux condenser showed a pressure of 20 atom. A portion of the condensate at the reflux condenser was discharged to the outside of the reaction system, and the remaining portion was refluxed into the reactor for the oxidation.

The solvent containing the specific catalytic was placed into the reactor at first. After the solvent was heated to a specific temperature while being stirred, 2,6-dimethylnaphthalene used as the raw material and the air was supplied, and the reaction product (a slurry) was continuously discharged so that the surface of the liquid in the reactor was kept at the same position. The reaction product which had been discharged was transferred into a tank which was equipped with a stirrer and adjusted to 80° C. by heating. The tank was open to the atmospheric pressure. The slurry discharged from the tank was supplied to a decanter type centrifuge and separated into a mother liquor of oxidation and wet crystals containing a portion of the mother liquor of oxidation. The mother liquor of oxidation was temporarily kept in a tank for the mother liquor of oxidation which was adjusted to 80° C. by heating and used in the following Examples and Reference Examples.

The entire amount or a portion of the mother liquor of oxidation in the tank for the mother liquor of oxidation was transferred to the preparation tank, and the remaining portion of the mother liquor of oxidation, when any portion remaining, was disposed. The recycled fraction of mother liquor of oxidation is defined as follows:

recycled fraction of mother liquor of oxidation=A/(A+B)×100 (%) wherein

A represents the amount (kg/h) of the mother liquor of oxidation transferred to the preparation tank, and B represents the amount (kg/h) of the disposed mother liquor of oxidation.

In the preparation tank, the solvent and the catalyst were supplemented into the mother liquor of oxidation to prepare the solvent having the above composition, and the prepared solvent was transferred to a tank for a heat treatment.

The tank for a heat treatment was made of titanium, equipped with a stirrer, and kept at a specific temperature by heating by an external heater. The time of the treatment in the tank for a heat treatment was adjusted by controlling the position of the surface of the liquid. The entire mother liquor of oxidation discharged from the tank for a heat treatment was recycled to the reactor for the oxidation.

In accordance with the above procedures for preparation, the recycled fraction of the mother liquor of oxidation, the temperature of the tank for a heat treatment, and the average residence time were varied, and 2,6-naphthalenedicarboxylic acid was produced. The content of crystals in the mother liquor of oxidation taken out from the tank for the mother liquor of oxidation was measured by the filtration method at specific time intervals.

The results of the measurement of the content of crystals in the mother liquor of oxidation are shown in Table 5.

TABLE 5

|  | Example | | | | Reference Example | |
| --- | --- | --- | --- | --- | --- | --- |
|  | 3 | 4 | 5 | 6 | 1 | 2 |
| recycled fraction of mother liquor (%) | 100 | 100 | 100 | 100 | 100 | 50 |
| tank for a heat treatment | | | | | | |
| temperature (° C.) | 200 | 220 | 160 | 160 | 80 | 130 |
| residence time (min) | 20 | 20 | 20 | 5 | 20 | 20 |
| time of operation (hr) | content of crystals in the mother liquor (%) | | | | | |
| 24 | 1.6 | 1.9 | 2.4 | 1.7 | 2.1 | 1.7 |
| 48 | 1.7 | 2.3 | 2.6 | 2.3 | 5.4 | 3.5 |
| 72 | 2.0 | 1.4 | 1.8 | 2.5 | 8.2 | 5.2 |
| 96 | 1.8 | 1.9 | 1.8 | 1.6 | 13.0 | 8.1 |
| 120 | 2.1 | 2.2 | 2.0 | 1.9 | 18.9 | 12.9 |

The results of the measurement of the content of crystals in the mother liquor of oxidation can be summarized as follows:

1) When the heat treatment was conducted at 130° C. (Reference Example 2), the content of crystals in the mother liquor of oxidation increased throughout the experiment although the recycled fraction of the mother liquor of oxidation was as low as 50%. In contrast, when the heat treatment was conducted at a temperature of 160° C. or higher as shown in Examples 3 to 6, the content of crystals in the mother liquor of oxidation stayed approximately the same while the operation proceeded. Therefore, the continuous operation could be conducted for a long period of time without any problem even at the recycled fraction of the mother liquor of oxidation of 100% when the heat treatment was conducted at 160° C. or higher.

2) When the average residence time was adjusted to 5 minutes by shifting the liquid surface in the tank for a heat treatment to a lower position (Example 6), the content of crystals in the mother liquor of oxidation stayed approximately the same while the operation proceeded. Therefore, the continuous operation could be conducted for a long period of time without any problem even at the recycled fraction of the mother liquor of oxidation of 100% when the heat treatment was conducted for 5 minutes or more.

What is claimed is:

1. A process for producing 2,6-naphthalenedicarboxylic acid comprising oxidizing 2,6-dimethylnaphthalene with a gas containing oxygen in a solvent comprising a lower aliphatic carboxylic acid in the presence of a catalyst comprising cobalt, manganese, and bromine, wherein the total amount of cobalt and manganese in the catalyst is 50 to 300 mg atom per 1 g mol of 2,6-dimethylnaphthalene, a ratio by g atom of manganese to cobalt in the catalyst is 10:1 to 6:1, and the oxidation is conducted at a temperature of 200 to 250° C.

2. A process according to claim 1, wherein the amount of bromine in the catalyst is 1 to 50 mg atom per 1 g mol of 2,6-dimethylnaphthalene.

3. A process according to claim 1, further comprising recycling 40% or more of a mother liquor obtained after separation of crystals of 2,6-naphthalenedicarboxylic acid from a product of the oxidation to a reactor for the oxidation.

4. A process according to claim 3, wherein the concentration of oxygen in a gas discharged from the reactor for the oxidation is 0.1 to 8% by volume based on a dry gas.

5. A process for continuously producing 2,6-naphthalenedicarboxylic acid comprising (a) oxidizing 2,6-dimethylnaphthalene with a gas containing oxygen in a solvent comprising a lower aliphatic carboxylic acid in the presence of a catalyst comprising cobalt, manganese, and bromine, (b) separating a mother liquor from a resultant slurry of a product of the oxidation in step (a) by a solid-liquid separation, (c) heating the mother liquor from step (b) at a temperature of 150° C. or higher and (d) recycling the heated mother liquor from step (c) to the oxidation in step (a).

6. A process according to claim 5, wherein 40% or more of the mother liquor separated in the solid-liquid separation is recycled.

7. A process according to claim 5, wherein the mother liquor is heated in step (c) for 3 minutes or more.

8. A process according to claim 5, wherein the concentration of oxygen in a gas discharged from a reactor for the oxidation is 0.5 to 5% by volume based on a dry gas.

9. A process according to claim 5, wherein the solid-liquid separation is conducted in a decanter centrifuge.

10. A process according to claim 1, wherein the lower aliphatic carboxylic acid is at least one acid selected from the group consisting of formic acid, acetic acid, propionic acid and butyric acid; and a ratio of the lower aliphatic carboxylic acid to the 2,6-dimethylnaphthalene is 1:1 to 20:1.

11. A process according to claim 10, wherein the ratio of the lower aliphatic carboxylic acid to the 2,6-dimethylnaphthalene is 2:1 to 12:1.

12. A process according to claim 10, wherein the ratio of the lower aliphatic carbocylic acid to the 2,6-dimethylnaphthalene is 2:1 to 10:1.

13. A process according to claim 12, wherein the total amount of cobalt and manganese in the catalyst is 100 to 250 mg atom per 1 g mol of the 2,6-dimethylnaphthalene.

14. A process according to claim 13, wherein the oxidation is carried out in a reactor at a pressure of 5 to 40 kg/cm²G and the concentration of oxygen in a gas discharged from the reactor is 0.5 to 5% by volume based on a dry gas.

15. A process according to claim 14, wherein the pressure is 10 to 30 kg/cm²G.

16. A process according to claim 6, wherein the total amount of cobalt and manganese in the catalyst is 30 to 300 mg atom per 1 g mol of the 2,6-dimethylnaphthalene; a ratio by g atom of the manganese to the cobalt in the catalyst is 10:1 to 6:1; and the amount of bromine in the catalyst is 1 to 500 mg atom per 1 g mol of the 2,6-dimethylnaphthalene.

17. A process according to claim 16, wherein the total amount of cobalt and manganese in the catalyst is 50 to 300 mg atom per 1 g mol of the 2,6-dimethylnaphthalene; and the amount of bromine in the catalyst is 10 to 300 mg atom per 1 g mol of the 2,6-dimethylnaphthalene.

18. A process according to claim 17, wherein the oxidizing in step (a) is carried out: in a reactor at a pressure of 5 to 40 kg/cm²G and at a temperature of 170 to 250° C.

19. A process according to claim 18, wherein in step (c), the heating is carried out: at a temperature of 160 to 240° C. for 3 minutes or more.

20. A process according to claim 19, wherein in step (b), the separating is carried out at atmospheric pressure and at a temperature of 50 to 110° C.

* * * * *